(12) United States Patent
Sands et al.

(10) Patent No.: US 8,100,281 B2
(45) Date of Patent: Jan. 24, 2012

(54) ORTHOPAEDIC INSTRUMENT STERILIZATION CASE

(75) Inventors: Daniel L. Sands, Warsaw, IN (US); Jon D. Shoemaker, Leesburg, IN (US); Chad M. LaMar, Carmel, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 1130 days.

(21) Appl. No.: 11/150,391

(22) Filed: Jun. 9, 2005

(65) Prior Publication Data

US 2005/0224384 A1    Oct. 13, 2005

Related U.S. Application Data

(63) Continuation-in-part of application No. 10/685,247, filed on Oct. 14, 2003, now Pat. No. 7,523,827.

(51) Int. Cl.
    *B65D 21/032*    (2006.01)
(52) U.S. Cl. ........ 220/326; 206/503; 312/217; 312/222; 312/311
(58) Field of Classification Search ............ 206/503
    See application file for complete search history.

(56) References Cited

U.S. PATENT DOCUMENTS

| 224,490 | A | 2/1880 | Sturges |
| 2,512,747 | A | 6/1950 | Lewis |
| 3,529,878 | A | 9/1970 | Blowers ................. 312/107 |
| 3,752,547 | A | 8/1973 | Propst et al. |
| 4,600,103 | A | 7/1986 | Tabler |
| 4,716,025 | A | 12/1987 | Nichols .................. 422/310 |
| 4,848,111 | A | 7/1989 | Franzen |
| 4,923,079 | A * | 5/1990 | Foy ........................ 220/7 |
| 5,078,460 | A | 1/1992 | Holsinger |
| 5,111,939 | A | 5/1992 | Schafer |
| 5,125,697 | A | 6/1992 | Kahl et al. |
| 5,176,281 | A | 1/1993 | Fiore |
| 5,287,980 | A | 2/1994 | Saltz |
| 5,424,047 | A | 6/1995 | Zwingenberger et al. .... 422/296 |
| 5,518,139 | A | 5/1996 | Trower et al. |
| 5,540,901 | A | 7/1996 | Riley ...................... 422/300 |
| 5,680,957 | A | 10/1997 | Liu |
| 5,740,906 | A | 4/1998 | Lai |
| 5,882,097 | A | 3/1999 | Kohagen et al. |

(Continued)

FOREIGN PATENT DOCUMENTS

EP    1 023 909 A1    8/2000

(Continued)

OTHER PUBLICATIONS

Supplementary European Search Report dated Jul. 17, 2009 in European Patent Application No. EP 06 75 0463 (5 pages).

(Continued)

*Primary Examiner* — Stephen Castellano
(74) *Attorney, Agent, or Firm* — Taylor IP, P.C.

(57) ABSTRACT

A sterilization case assembly including a plurality of sterilization cases having a first sterilization case and a second sterilization case. The second sterilization case is stacked upon the first sterilization case in a vertical direction. The second sterilization case is offset from the first sterilization case in a direction transverse to the vertical direction. In another embodiment, the second sterilization case is configured for both stacking offset from the first sterilization case in a direction transverse to the vertical direction and stacking inline from the first sterilization case in a direction transverse to the vertical direction.

12 Claims, 11 Drawing Sheets

U.S. PATENT DOCUMENTS

| | | | | |
|---|---|---|---|---|
| 5,893,618 | A | 4/1999 | LePage, Jr. et al. | 312/265.6 |
| 6,116,452 | A | 9/2000 | Hamel et al. | 220/318 |
| 6,164,738 | A | 12/2000 | Dane et al. | 312/311 |
| 6,368,565 | B1 | 4/2002 | Michaelson et al. | 422/300 |
| 6,395,234 | B1 | 5/2002 | Hunnell et al. | |
| 6,896,149 | B1 | 5/2005 | Berry, III | 220/4.28 |
| 6,932,444 | B2 | 8/2005 | Price | |
| 6,935,710 | B2 * | 8/2005 | Chen et al. | 312/333 |
| 7,219,969 | B2 * | 5/2007 | Bezzubov | 312/107 |
| 7,523,827 | B2 | 4/2009 | Dane et al. | |
| 2002/0064490 | A1 | 5/2002 | Michaelson et al. | 422/300 |
| 2004/0129595 | A1 | 7/2004 | Dane et al. | |
| 2004/0135477 | A1 | 7/2004 | Price | |
| 2004/0169447 | A1 | 9/2004 | Bezzubov | |
| 2004/0174100 | A1 | 9/2004 | Chen et al. | |

FOREIGN PATENT DOCUMENTS

| | | |
|---|---|---|
| EP | 2 216 053 B1 | 8/2011 |
| JP | 10-252313 | 9/1998 |
| JP | 3096023 U | 8/2003 |

OTHER PUBLICATIONS

Office Action dated Aug. 10, 2009 in European Patent Application No. EP 06 75 0463.9 (4 pages).
Documents regarding PCT/US2006/014435 (11 pages): Notification of Transmittal of International Preliminary Report on Patentability; International Preliminary Report on Patentability; Notification of Transmittal of International Search Report and Written Opinion of International Searching Authority, or Declaration; International Search Report; Written Opinion of International Searching Authority.
Office Action dated Apr. 4, 2009 from the Patent Office of the People's Republic of China in Patent Application No. 200680025998.4 (7 pages).
Office Action dated May 28, 2009 from Canadian Intellectual Property Office in Patent Application No. 2,611,692 (2 pages).
Office Action dated Jan. 8, 2010 from the Patent Office of the People's Republic of China in Patent Application No. 200680025998.4 (4 pages).
Office Action dated Jan. 29, 2010 in U.S. Appl. No. 11/411,649.
English translation of Office Action dated Apr. 24, 2009 from the Patent Office of the People's Republic of China for Application No. 200680025998.4 (7 pages).
Communication dated Apr. 6, 2011 from European Patent Office in Application No. EP 10 000 204.7-2113 (36 pages).
Office Action dated Apr. 11, 2011 from Canadian Intellectual Property Office for Application No. 2,611,692 (3 pages).
Office Action dated May 31, 2011 from the Patent Office of the People's Republic of China for Application No. 2011052600294390 (2 pages).
Communication dated Jul. 13, 2011 from European Patent Office in Application No. EP 10 007 775.9-2113 (3 pages).
Extended European Search Report dated Sep. 21, 2010 from European Patent Office in European patent application No. 10007775.9-2113 (5 pages).
English translation of Office Action of Aug. 16, 2010 from Japanese Patent Office in Japanese patent application No. 2008-515694 (2 pages).
Office Action dated May 25, 2010 of Canadian Intellectual Property Office in application No. 2,611,692 (3 pages).
Office Action dated Apr. 12, 2010 of European Patent Office in application No. 06 750 463.9-2113 (4 pages).
Office Action dated Apr. 13, 2010 of European Patent Office in application No. 10 000 204.7-2113 (3 pages).
Communication dated Jun. 21, 2010 of European Patent Office in application No. 10 000 204.7-2113 (6 pages).
Communication dated Oct. 7, 2010 of European Patent Office in application No. 10 000 204.7-2113 (8 pages).
Office Action dated Jan. 28, 2011 from the Peoples Republic of China for Chinese Patent Application No. 200680025998.4 and English language document entitled "Summary of the Third Office Action" related to this Office Action (4 pages).
English language document entitled "Notification of Reasons for Refusal (Office Action)" concerning Office Action drafted on Jan. 12, 2011 and reported on Feb. 7, 2011 from the Japanese Patent Office for Japanese Patent Application No. 2008-515694 (1 page).
English machine translation of JP-U-3096023 (10 pages).
English machine translation of JP 10-252313, including Patent Abstract of Japan (12 pages).
Office Action of Japanese Patent Office drafted on Aug. 22, 2011 and mailed on Aug. 24, 2011 for Japanese Patent Application No. 2008-515694 (2 pages), and English summary of this Office Action (1 page).
Communication dated Jul. 28, 2011 for European Patent Application No. 10000204.7-2113 (1 page).

* cited by examiner

ORTHOPAEDIC INSTRUMENT STERILIZATION CASE

CROSS REFERENCE TO RELATED APPLICATIONS

This application is a continuation-in-part of U.S. patent application Ser. No. 10/685,247, entitled "ORTHOPAEDIC INSTRUMENT STERILIZATION CASE," filed Oct. 14, 2003, now U.S. Pat. No. 7,523,827.

BACKGROUND OF THE INVENTION

1. Field of the Invention

The present invention relates to sterilization cases and, more particularly, to orthopaedic instrument sterilization cases.

2. Description of the Related Art

Sterilization containers are known that provide organization, storage and sterilization functionality for surgical instruments and devices. In order to avoid infection to a patient on which such instruments used, the instruments are required to be cleaned and sterilized after a procedure, and therefore, before use.

Surgical procedures are regularly performed using "sets" of pre-selected surgical instruments, each set being a collection of instruments established from experience or design to be useful in a given surgical procedure. The surgical instruments expected to be used in a particular procedure are grouped together to form a set, and, as a set, are sterilized, stored on a pan or tray, and finally transported on that pan or tray to the operating room when their use is required. Complex procedures typically involve a substantial number of instruments. Thus, typically, several instrument trays may be necessary to accommodate all of the required surgical instruments. Accordingly, sterilizing cases often are designed to accommodate a plurality of trays with the instruments arranged on the trays in such a manner that the trays may be accessed as the surgical procedure advances often in a preset sequence.

An example of a cleaning procedure can be the instruments are first placed into a tank containing water and perhaps solvents, and ultrasound is applied to agitate the fluid to wash and remove the debris, such as biomatter, remaining on the instruments from their last use. The instruments are then sterilized in some manner to destroy any microorganisms, viruses or other contamination on the hand instruments. The two sterilization methods include the use of dry heat, wherein the instruments are heated to a high temperature, for example at least 365° Fahrenheit for a period of time, or the use of steam under pressure in an autoclave system. The time to sterilize, using a steam autoclave system, depends on heat and pressure and whether the instruments are wrapped or not. In some sterilization processes, chemicals are applied to the hand instruments as an intermediate step between the ultrasonic bath and the heating. A third method of sterilization is a chemical autoclave wherein a controlled atmosphere of various gases is used, with heat and humidity in some instances, to sterilize the instruments held within sealed sterile wraps. Radiation can also be used to sterilize instruments. In the situation of instruments in a sterilization case, a sterile wrap can cover the case to maintain the sterile field within the case after sterilization.

Major surgeries such as hip or knee replacements have larger instruments requiring multiple cases and trays of instruments. Sterilization systems are known which have multiple trays in a drawer arrangement, however when a tray is pulled forward to access the instruments, there is a shift in center of gravity forward which can cause the system to become unstable and tilt forward. Braces are known which rotate forward to stabilize such a sterilization case. Such braces, when in a stabilizing position, increase the footprint of the sterilization case on the table in the operating room.

What is needed in the art is an easily configurable sterilization system which does not become unstable when accessing instruments, which can accommodate large and complex instrument sets and which minimizes the sterilization container footprint while maximizing access to the instruments.

SUMMARY OF THE INVENTION

The present invention provides sterilization container which are configurable into a multiple level, stair step and/or inline stacked, self-contained and self-standing instrument case for sterilizing, organizing, containing and transporting of surgical instruments and devices.

The invention comprises, in one form thereof, a sterilization case assembly including a plurality of sterilization cases having a first sterilization case and a second sterilization case. The second sterilization case is stacked upon the first sterilization case in a vertical direction. The second sterilization case is offset from the first sterilization case in a direction transverse to the vertical direction.

The invention comprises, in another form thereof, a sterilization case assembly including a plurality of sterilization cases having a first sterilization case and a second sterilization case. The second sterilization case is stacked upon the first sterilization case in a vertical direction. The second sterilization case is configured for both stacking offset from the first sterilization case in a direction transverse to the vertical direction and stacking inline from the first sterilization case in a direction transverse to the vertical direction.

The invention comprises, in another form thereof, a sterilization case assembly including a plurality of sterilization cases having a first sterilization case with a first lid and a second sterilization case with a second lid. The second sterilization case is stacked upon the first sterilization case in a vertical direction. Both of the first sterilization case and the second sterilization case are configured for stacking both with at least one of the first lid and the second lid and in the absence of at least one of the first lid and the second lid.

The invention comprises, in another form thereof, a sterilization case including a drawer having a latch mechanism. A lid is connected to the drawer. The lid has a latch receiver which receives the latch mechanism when both the lid is in a closed position and the drawer is in a closed position.

The invention comprises, in another form thereof, a sterilization case including at least one end cap having an inside contour. At least one inside contour has a locking bracket. A drawer is slidably connected to the end cap. The drawer includes at least one resilient lever with an aperture. At least one locking bracket is received in a corresponding aperture when the drawer is in a closed position.

An advantage of the present invention is an easily configurable sterilization system which does not become unstable when accessing instruments.

Another advantage of the present invention is a sterilization system which can accommodate large and complex instrument sets and which minimizes the sterilization system footprint while maximizing access to the instruments.

Yet another advantage of the present invention is a stair step type stacking of individual cases acts to offset center of gravity shifts to prevent tipping when accessing instruments.

A further advantage of the present invention is a slidable modular mounting that allows removal of a tray from a drawer.

A further advantage of the present invention is four to six levels of sterilization trays stacked vertically will only require/occupy the same space that was once used by fewer trays.

A further advantage of the present invention is that the amount of space required in the operating room for sterilization cases and trays is decreased.

A further advantage of the present invention is that it enables a secure modular arrangement of single level trays of instruments that improves organization, presentation, access and deployment of instruments.

Another advantage of an embodiment of the present invention is a hinged front cover which locks in the open position to provide additional stabilization to prevent tipping.

A further advantage of the present invention is that the sterilization cases can be stacked either inline or offset.

A further advantage of the present invention is that the sterilization cases can be stacked with or without their corresponding lids.

A further advantage of the present invention is that the sterilization cases have secure latching of both the lid and the drawer to hold each closed when appropriate.

Another advantage of the present invention is that the sterilization cases have secure latching of the drawer with lid closed, opened or removed.

Another advantage of the present invention is that the sterilization cases can be stacked offset for surgical use to prevent tipping when drawers are open, and then stacked inline for storage, cleaning and/or sterilization use.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
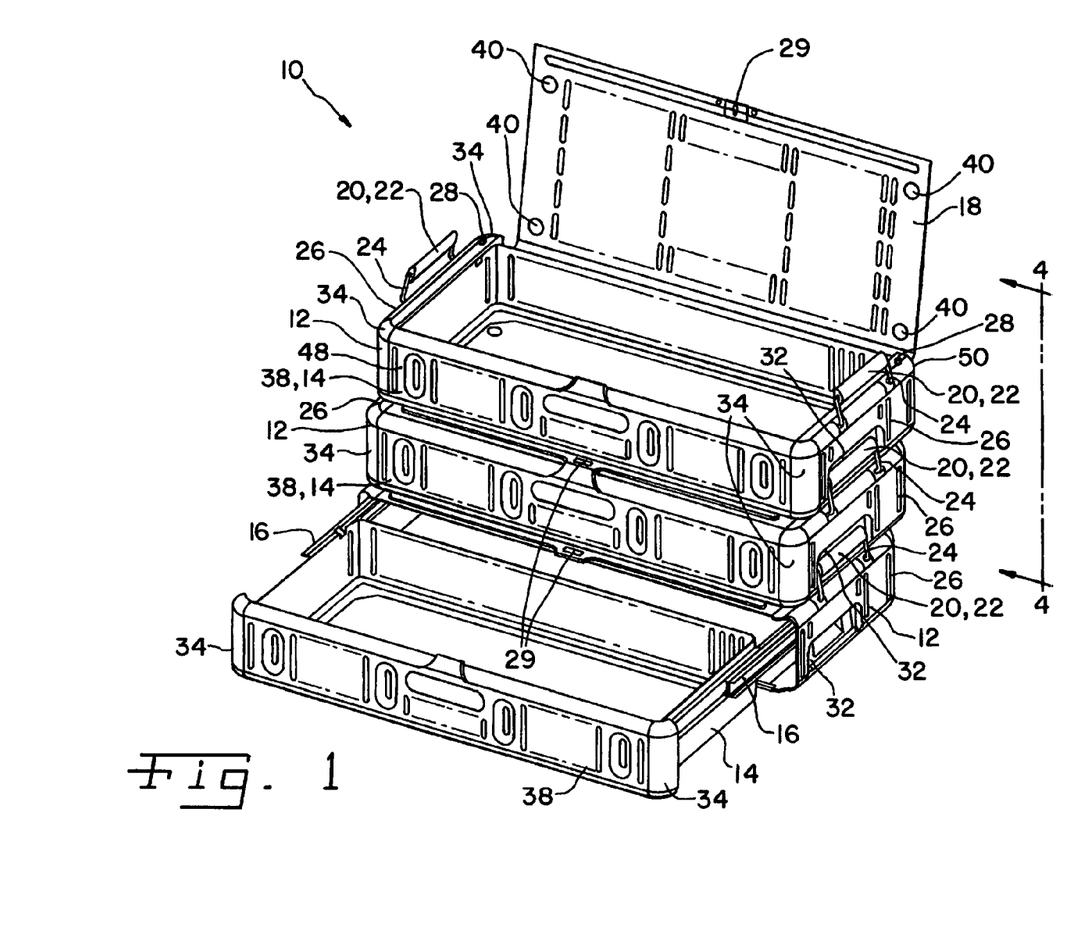
FIG. 1 is a perspective view of an embodiment of a multiple level sterilization system of the present invention, including 3 stacked cases.

Referring now to the drawings, and more particularly to FIG. 1, there is shown a stacked sterilization case assembly or system 10 which generally includes a plurality of sterilization cases 12, and in the embodiment shown, specifically three sterilization cases 12. Each sterilization case 12 includes at least one drawer 14 therein and attached to sterilization case 12 using slide mechanisms 16. Each sterilization case 12 includes lid 18 which can pivot open as shown. As will be subsequently discussed in detail, only one of drawer 14 or lid 18 can be open for a given sterilization case 12. The trays are interlocked using at least one handle 20 that can be located on both of the side of the trays. At least one sterilization case 12 is offset from another sterilization case 12 in a direction transverse to the vertical direction such as a frontward to reward direction as shown in the drawings.

Figure 2:
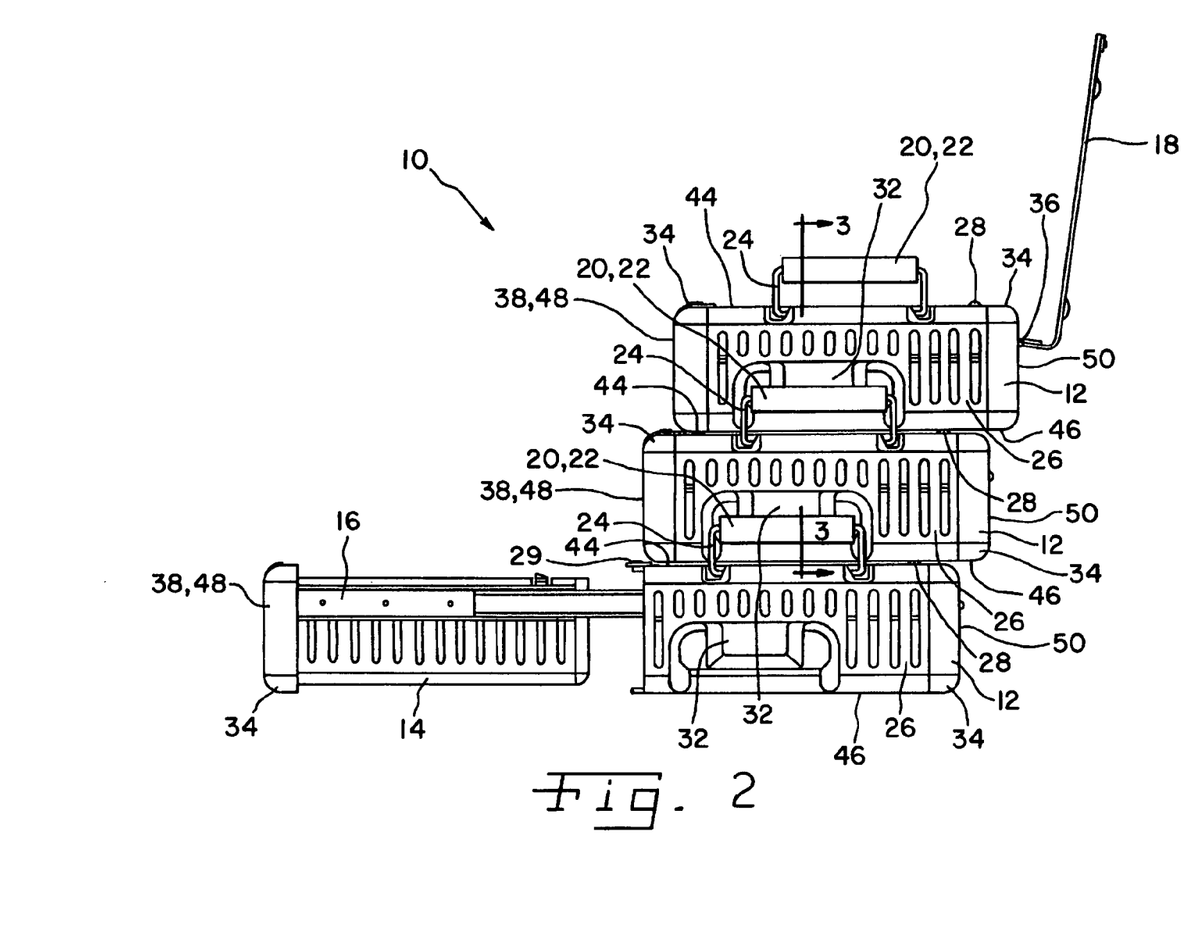
FIG. 2 is a side view of the multiple level sterilization case of FIG. 1.

FIG. 2 illustrates how the offset stacking features conserve back table space and help prevent tipping as drawers are opened and closed. As shown, lid 18 is capable of rotation, whereas drawer 14 is capable of translation.

Ergonomic handle grips 22 can be soft and cool to the touch. Unique bail 24 shape allows handles to lay flat on a case top or swing upward to facilitate proper removal technique from closed container systems. Resilient handle grips 22 roll flat in the palm of the hand for comfortable lifting and roll over center and into end cap 26 to lock stacked cases together.

Safety catch 28 prevents drawer 14 from opening in sterilization case 12 unless another sterilization case 12 is stacked upon it. The contents of a single case or the top case in a stack are accessed by opening lid 18. Safety catch 28 allows a drawer to be released in a sterilization case 12 having another sterilization case 12 stacked upon it when safety catch 28 is actuated. Latch 29 interlocks lid 18 and drawer 14, and when slid towards the back (away from the drawer front) of sterilization case 12, depending on the state of safety catch 28 and whether another case is on lid 18, one of drawer 14 or lid 18 will open.

Figure 3:
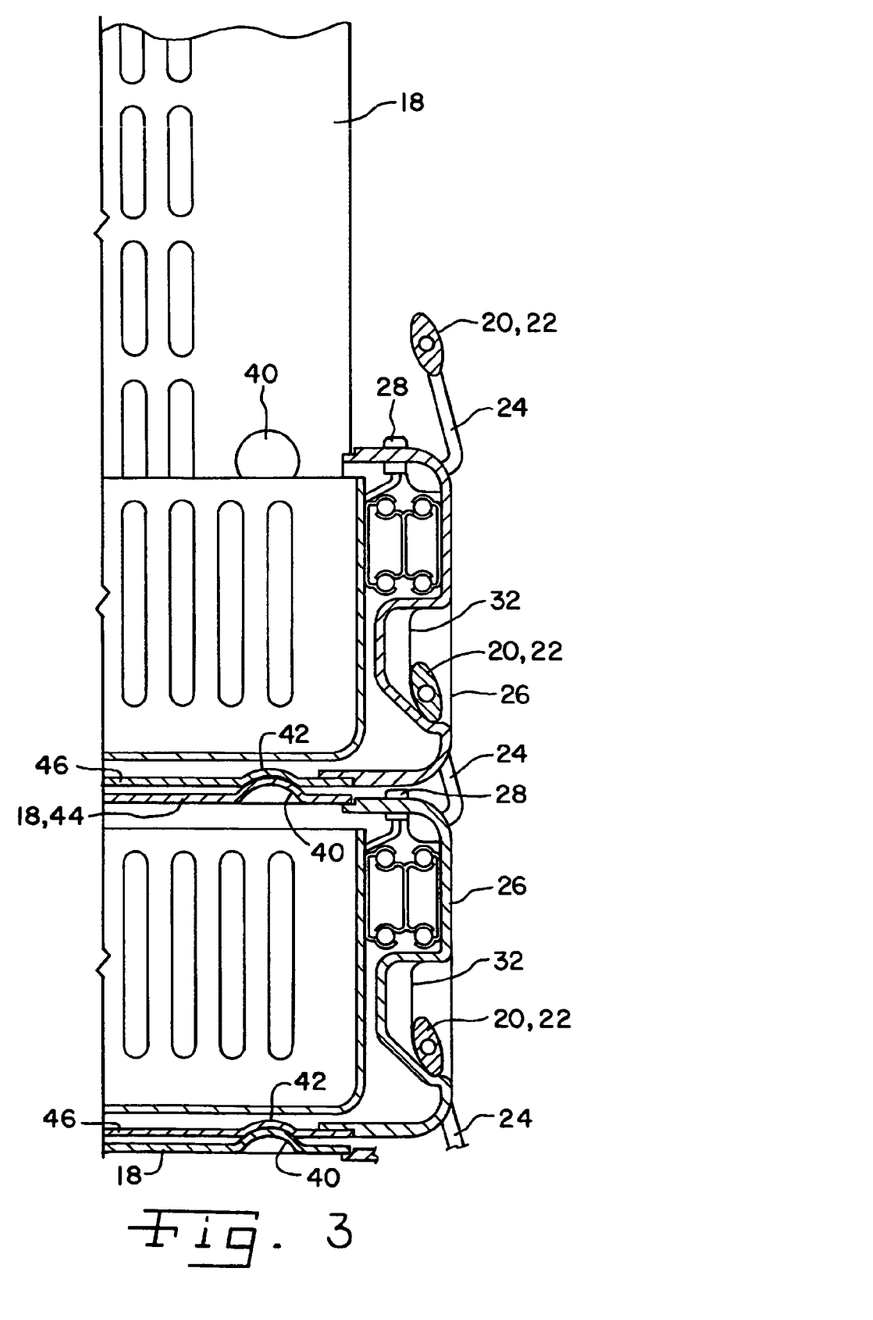
FIG. 3 is a fragmentary cross-sectional view taken along section line 3-3 of FIG. 2.

The present invention can include assist spring 30 that slightly opens drawer 14 of a lower stacked case, or lid 18 of single cases or the top case in a stack. Assist spring 30 is shown for drawer 14, the assist spring 30 for a lid can be similar to what is shown, but positioned differently to actuate lid 18. Assist spring 30 can be a variety of resilient members such as other spring types (coil spring, etc.), rubber items and flexible containers with compressible liquids therein. Assist spring 30 facilitates easy opening of drawers 14 and lids 18.

Drawers 14 can hold plastic trays by their rims and metal inserts as drop-ins, such trays and inserts holding sets of instruments (all not shown).

The size and shape of sterilization case 12 is wrap and container friendly and features resilient carrying handles 20 and recessed carrying pockets 32 in end panels 26. Rounded corners 34 are less likely to puncture a sterile wrap than sharp corners.

Take-away hinges 36 allow removal of the lid for access or cleaning purposes. End panels 26 can be cast from aluminum, titanium or other suitable metals, or injection molded from Radel, PEEK or other suitable plastics or materials.

Slider mechanisms 16 can be stainless steel or other suitable materials and can be rated to hold 40 lbs per pair, although different load carrying capacity is possible based on the expected use of sterilization system 10. Drawer front 38 can be drawn from aluminum or vacuum formed from Radel or made from other suitable materials. The highly perforated design with open drawer bottom and ability to access contents from the top or through an open drawer ensures unsurpassed cleanability and sterilization and safe access to contents.

Figure 4:
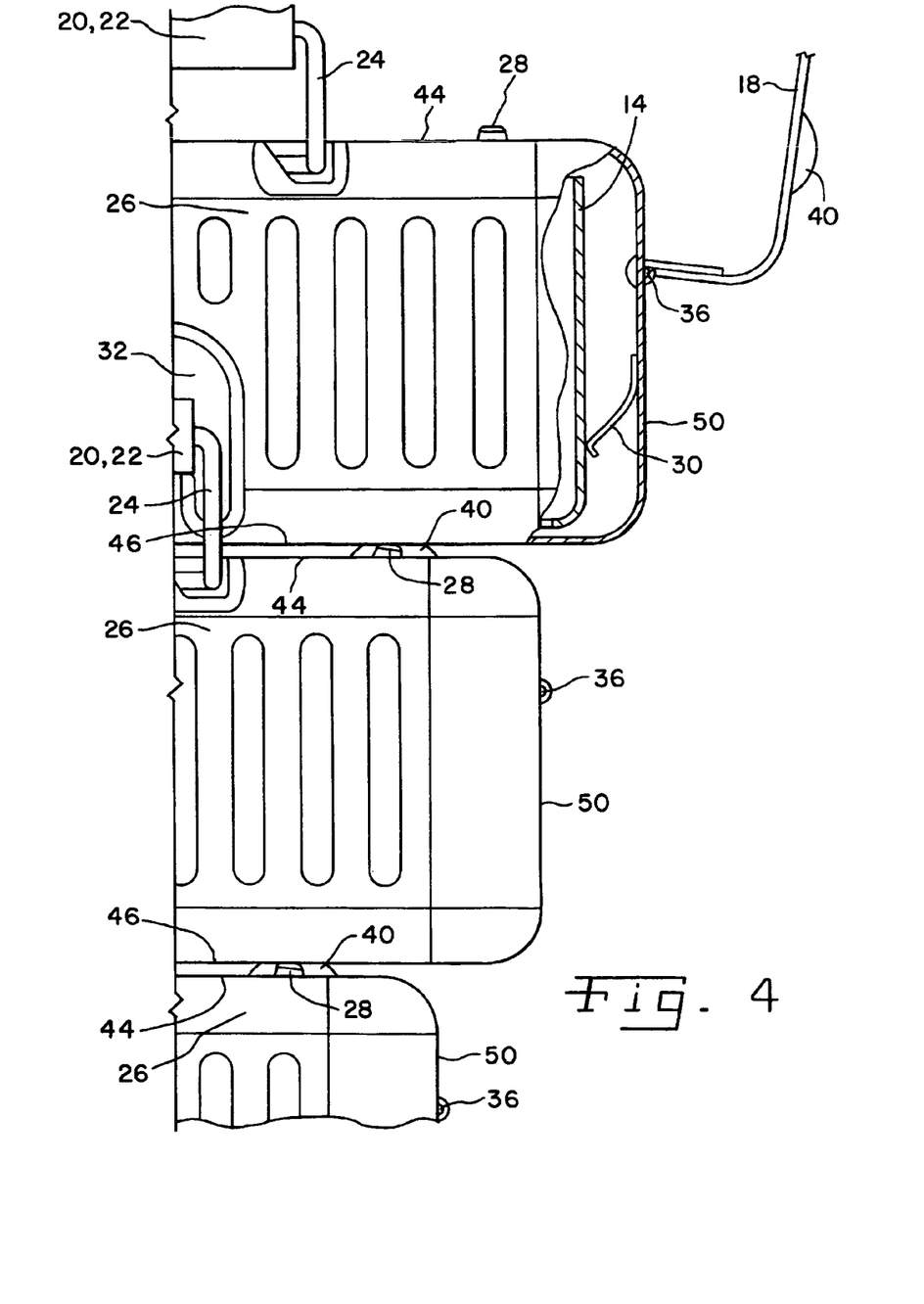
FIG. 4 is a partially fragmentary side view as viewed along section line 4-4 of FIG. 1.

The top 44 of sterilization case 12, or lid 18, includes at least one top registration element 40. Bottom 46 of sterilization case 12 includes at least one bottom registration element 42. At least one top registration element 40 is offset from at least one bottom registration element 42 in a direction parallel with bottom 46, or alternatively, lid 18 when closed. For example, sterilization case 12 includes opposed sides, first side 48 and second side 50, connected to bottom 46. At least one bottom registration element 42 is closer to one opposed side than at least one top registration element 40.

Figure 5:
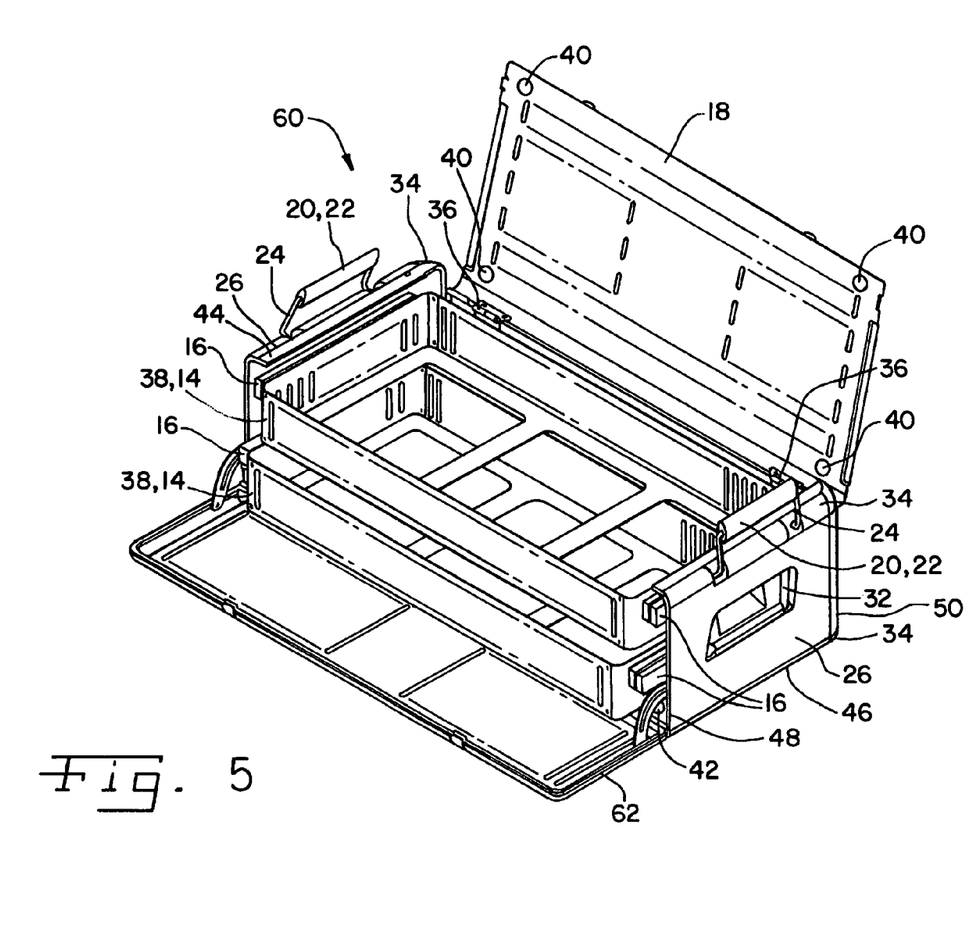
FIG. 5 is a perspective view of another embodiment of a stackable sterilization case having multiple trays.

In another embodiment (FIG. 5), sterilization case 60 includes a plurality of drawers 14 and hinged front cover 62. Hinged front cover 62 can also be lockable. Sterilization case 60 can be offset stacked similarly to sterilization case 12. Other features are similar to as already described and have been given identical reference characters. Sterilization case 60 may be more suitable for a hip or knee replacement surgery whereas sterilization case 12 may be more suitable for spinal or extremities surgery.

In use, a second sterilization case 12 is stacked upon a first sterilization case 12 in a vertical direction, and concurrently, the second sterilization case 12 is offset from the first sterilization case 12 in a direction transverse to the vertical direction. The second sterilization case 12 can be interlocked with the first sterilization case 12 using handles 20 and corresponding recessed pockets 32.

Figure 6:
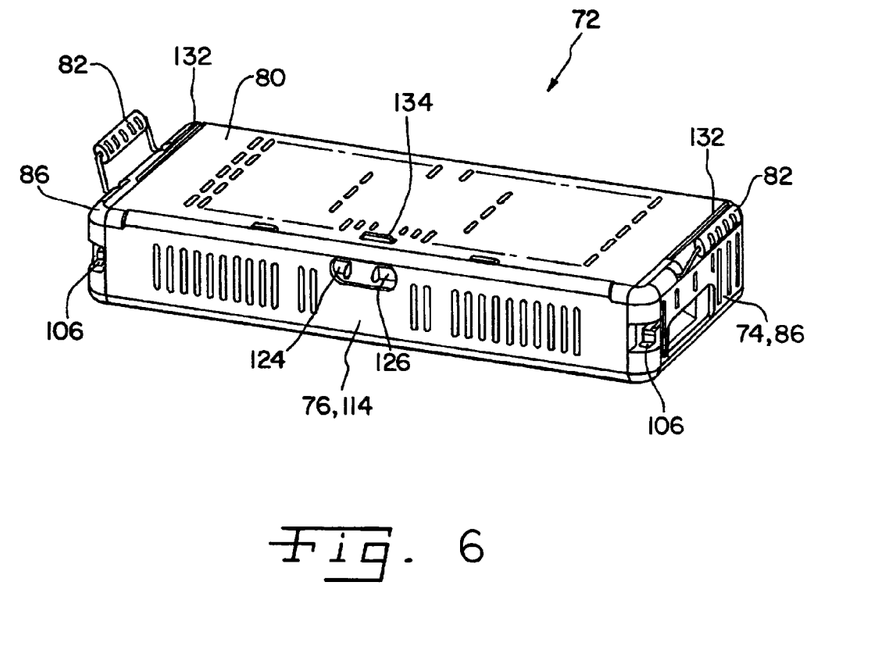
FIG. 6 is a perspective view of another embodiment of a stackable sterilization case.
Figure 7:
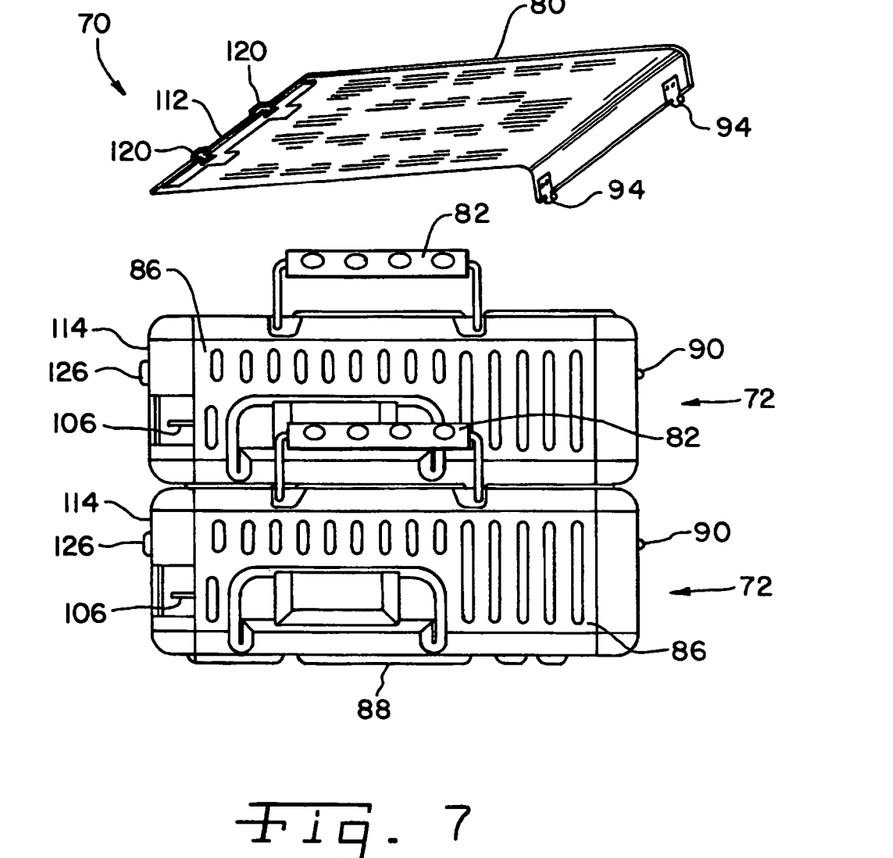
FIG. 7 is a side view of another embodiment of a sterilization case assembly illustrating the in line stacking of the sterilization cases of FIG. 6, and also showing a lid, in perspective, removed from a sterilization case.

Referring now to FIGS. 6-12, and, more particularly to FIGS. 6 and 7, there is shown a stacked sterilization case assembly or system 70 which generally includes a plurality of sterilization cases 72. Sterilization case assembly or system 70 and sterilization cases 72 can generally be used to contain, organize and sterilize one or more surgical instruments (not shown) or sets or trays thereof, in particular orthopaedic instruments in a surgical, cleaning, sterilization or storage environment. Sterilization case assembly or system 70 and sterilization cases 72 can generally include the elements described above and illustrated in FIGS. 1-5, and in addition to being offset stackable as illustrated in FIGS. 1-5, sterilization case assembly 70 and sterilization cases 72 can be stackable inline in a direction transverse to the vertical direction, as shown in FIG. 7.

Sterilization case 72 includes a base 74, and at least one drawer 76 therein and attached to base 74 using slide mechanisms 78. Sterilization case 12 includes lid 80 which can pivot open, and additionally, can be removed. Consequently, sterilization cases 12 can be stacked, either offset or inline, with all of the corresponding lids 80 installed on their respective sterilization case 12, or alternatively, with any or all of the lids 80 removed from their respective sterilization case 12. Sterilization case 12 includes handle 82 which can be used to interlock sterilization cases 12 when they are stacked offset as described above; however, handles do not engage to interlock sterilization cases 12 when they are stacked inline, to prevent misuse. Sterilization case 12 is configured for stacking with at least one other sterilization case 12 both offset and inline in a direction transverse to the vertical direction.

Figure 8:
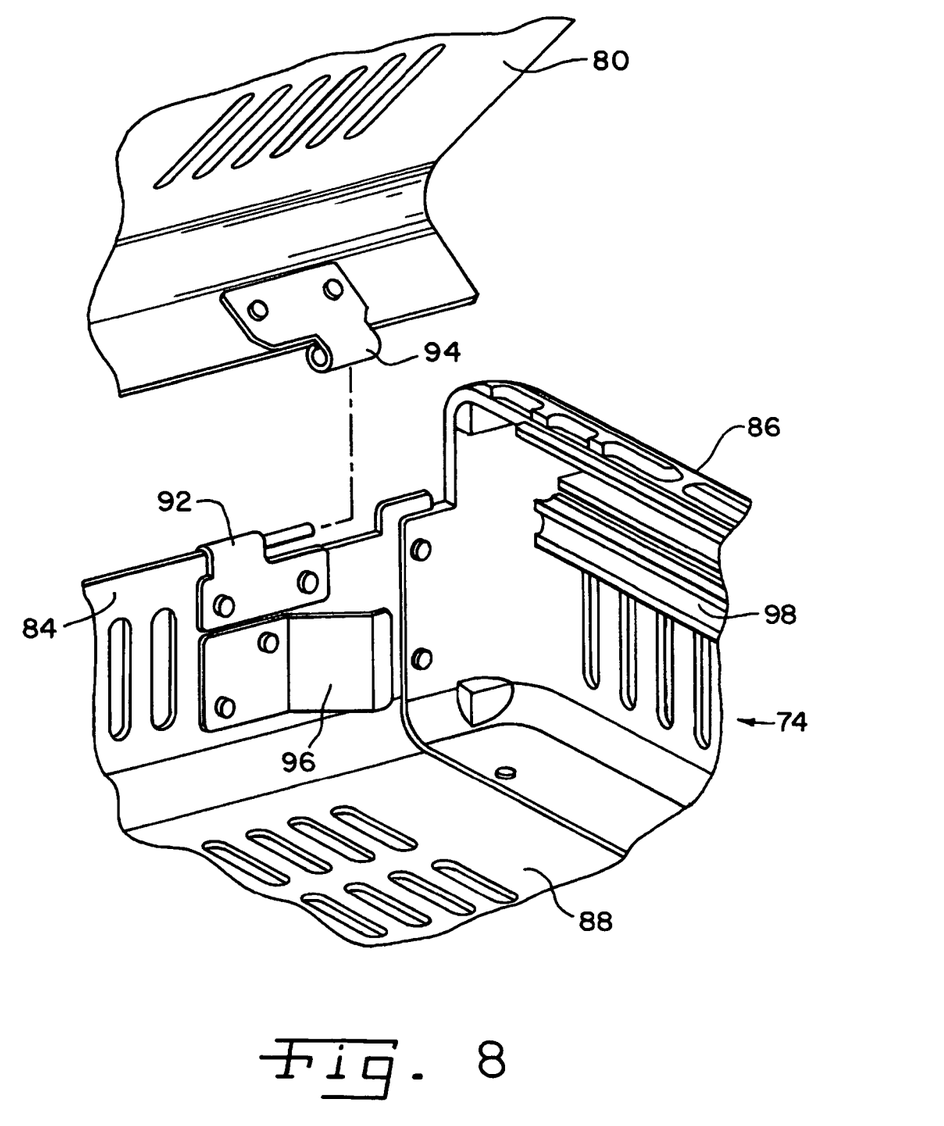
FIG. 8 is a perspective, partially exploded and fragmentary view of a rear corner of the sterilization case of FIG. 6, illustrating the take away hinge which allows easy removal of the lid from the sterilization case.
Figure 11:
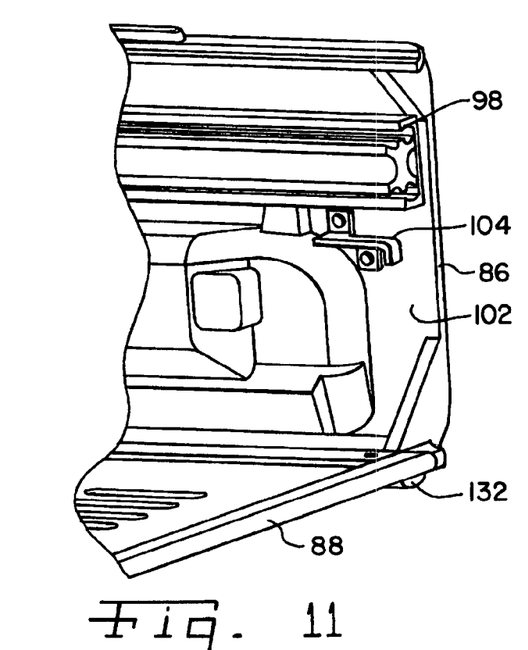
FIG. 11 is a perspective and fragmentary view of the side of the base (end cap) of the sterilization case of FIG. 6, illustrating the drawer latching mechanism, and in particular, the locking bracket of the drawer latching mechanism corresponding to the drawer latching mechanism of FIG. 10.

Base 74 generally includes back 84, end caps 86 and bottom 88. Back 84 includes at least one hinge post 92 of take-away hinge 90 for lid 80, and will generally include two hinge posts 92 which mate with corresponding hinge receivers 94 on lid 80. Back 84 can also include resilient member 96 which can be used to bias drawer 76 such that drawer 76 will open slightly when unlatched. Each end cap 86 is connected to a base rail 98 of a corresponding slide mechanism 78. End caps 86 include an inside contour or surface 102 with a locking bracket 104. A handle 82 can be attached to each of end caps 86. Handles 82 can be injection molded with two halves which snap together around a preformed wire or bail. Handles 82 offer ergonomic design for lifting/handling and lock cases 72 together when cases 72 are offset stacked.

Figure 9:
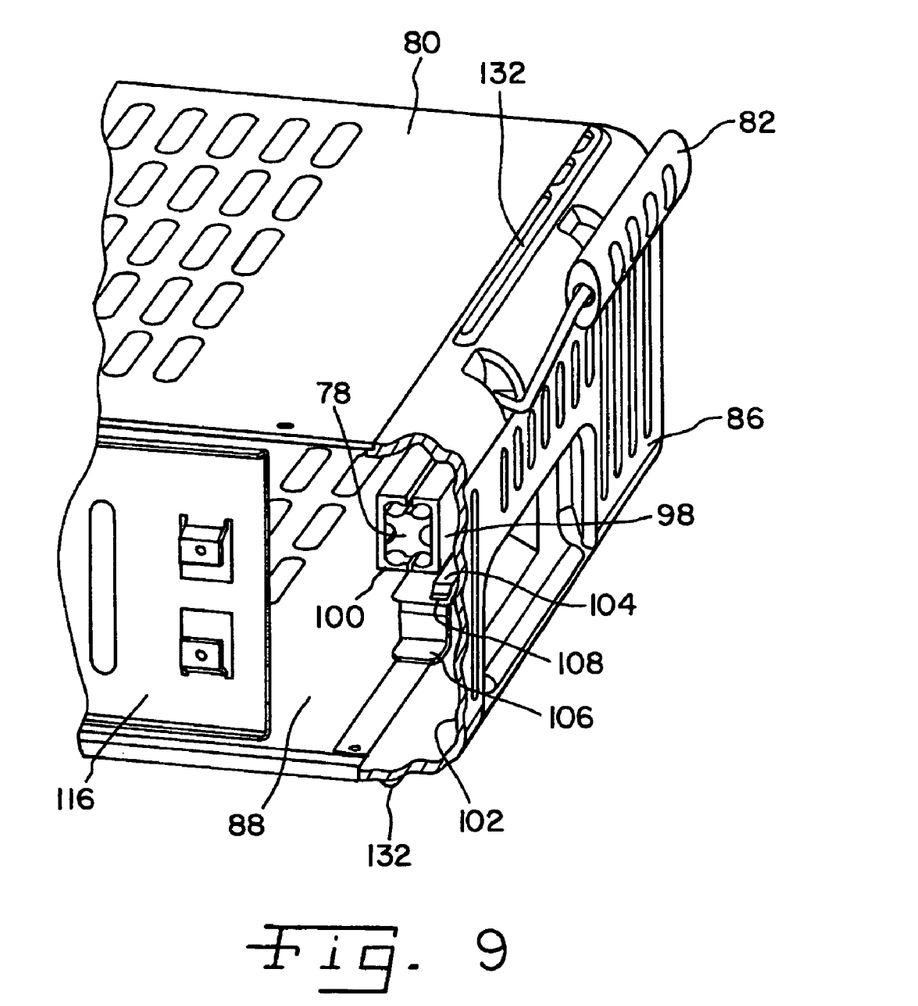
FIG. 9 is a perspective and fragmentary view of the side of the sterilization case of FIG. 6, illustrating the drawer latching mechanism in particular.
Figure 10:
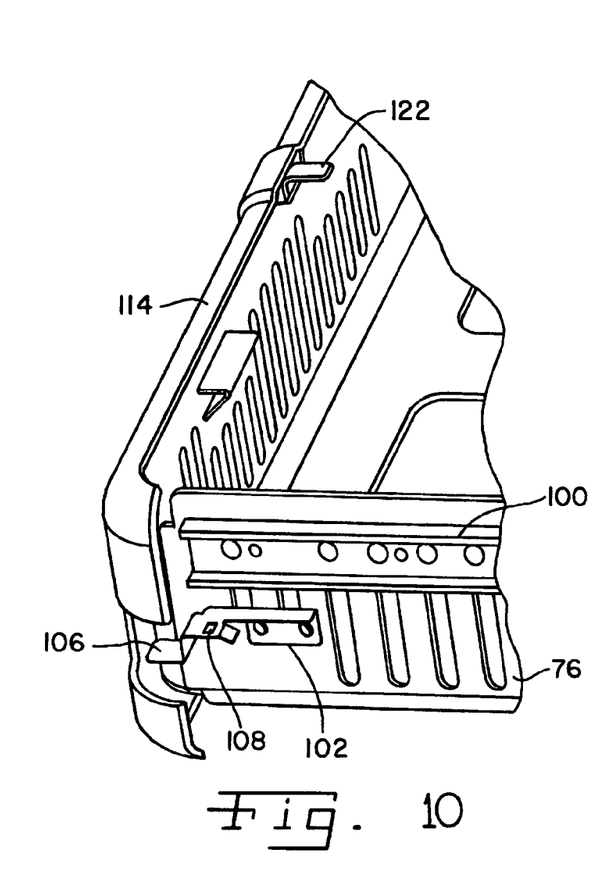
FIG. 10 is a perspective and fragmentary view of the side of the drawer of the sterilization case of FIG. 6, illustrating the drawer latching mechanism, and in particular, the resilient lever of the drawer latching mechanism.

Drawer 76 is slidably connected to an end cap 86 on either side of drawer 76 via slide mechanisms 78, and in particular, drawer 76 connects to drawer rail 100 of slide mechanisms 78. On at least one side of drawer 76 there is included resilient lever 106 with aperture 108. The drawer 76 latch mechanism primarily includes at least one locking bracket 104 which are received in a corresponding aperture 108 when drawer 76 is in a closed position. The drawer latches are therefore single action and are shown on both sides of case 72. A push down on resilient lever 106 with the thumb or other appendage and resilient lever 106 releases from locking bracket 104 to allow drawer 76 to move forward, which movement can be aided by resilient member 96.

The two rails 98, 100 of slide mechanism 78 can be unlubricated aluminum with stainless steel ball bearings and added steam holes for sterilization and cleanability, for example.

Figure 12:
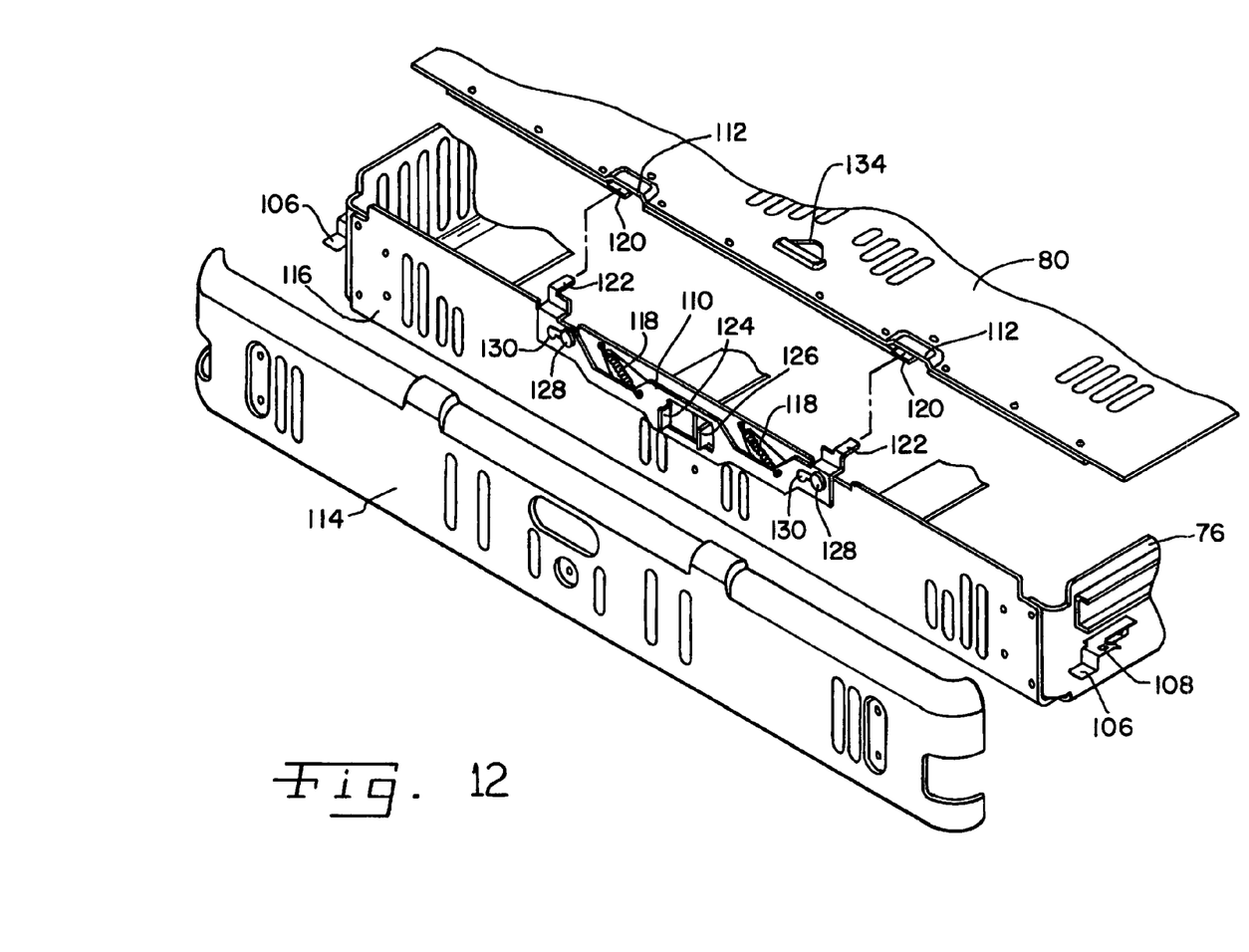
FIG. 12 is a perspective, partially exploded and fragmentary view of the front of the drawer and lid of the sterilization case of FIG. 6, illustrating the lid latching mechanism in particular.

The lid latching mechanism includes latch mechanism 110 on drawer 76 and at least one latch receiver 112 on lid 80. Latch mechanism 110 is received in latch receivers 112 when both lid 80 and drawer 76 are in a closed position. More particularly, drawer 76 includes a drawer front 114 with a front panel 116. Latch mechanism 110 is slidably connected to front panel 116. At least one resilient member 118 biases latch mechanism 110 with respect to front panel 116 to a closed position. In the embodiment shown, latch mechanism 110 is slidable in a direction approximately parallel to front panel 116. Latch receiver 112 includes at least one slotted ledge 120. Latch mechanism 110 includes at least one clasp 122 positioned transverse to the sliding direction of latch mechanism 110 and is received in a corresponding slotted ledge 120 when both lid 80 and drawer 76 are in a closed position. Latch mechanism tab 124 is connected to latch mechanism 110 and front panel tab 126 is connected to front panel 116. Latch mechanism 110 is connected to front panel 116 via fasteners 128 which allow latch mechanism 110 to slide relative to front panel 116 in slots 130 of latch mechanism 110. This unique lid latching allows single handed operation. Pinching or compressing tabs 124 and 126 together disengages lid 80, and lid 80 can be pivoted open and removed, if desired, by sliding lid 80 laterally thereby releasing hinge receiver 94 from hinge post 92. Detent 134 can be used to pivot lid 80 upward and remove when lid 80 is unlatched. Drawer 76 can be opened or closed with lid 80 closed, open or completely removed.

Ribs 132 enable a positive location and feel to stack and nest multiple cases 72. Ribs 132 allow cases 72 to be stacked inline for storage, cleaning and/or sterilization, and/or offset when in surgical or other use, when drawers 76 may be opened, to prevent tipping.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A sterilization case, comprising:
   at least one end cap having an inside surface including a locking bracket; and
   a drawer slidably connected to said end cap, said drawer including at least one lever having an aperture, at least one said locking bracket being received in a corresponding said aperture when said drawer is in a closed position.

2. The sterilization case of claim 1, wherein said at least one lever is at least one resilient lever.

3. The sterilization case of claim 1, wherein said drawer includes at least one end panel, said at least one lever is located on said at least one end panel.

4. A sterilization case, comprising:
   a drawer having a front panel and a latch mechanism, said front panel including a first tab, said latch mechanism being connected to said front panel and including a second tab which is configured for moving toward said first tab, said latch mechanism including an aperture through which said first tab of said front panel extends; and
   a lid being connected to said drawer, said lid having a latch receiver receiving said latch mechanism when both said lid is in a closed position and said drawer is in a closed position.

5. The sterilization case of claim 4, wherein said drawer includes a drawer front with said front panel, said latch mechanism being slidably connected to said front panel.

6. The sterilization case of claim 5, further including a resilient member biasing said latch mechanism with respect to said front panel.

7. The sterilization case of claim 5, wherein said latch mechanism is slidable in a direction approximately parallel to said front panel.

8. The sterilization case of claim 7, wherein said latch receiver includes at least one slotted ledge.

9. The sterilization case of claim 8, wherein said latch mechanism includes at least one clasp positioned transverse to said direction and received in a corresponding said at least one slotted ledge when both said lid is in a closed position and said drawer is in a closed position.

10. The sterilization case of claim 4, further including an end cap, wherein said drawer is slidably connected to said end cap.

11. The sterilization case of claim 10, wherein said drawer is slidably connected to said end cap with an unlubricated slide rail.

12. The sterilization case of claim 4, wherein said lid is pivotably connected to said drawer.

* * * * *